US008912141B2

(12) United States Patent
Halfon

(10) Patent No.: US 8,912,141 B2
(45) Date of Patent: Dec. 16, 2014

(54) TREATMENT OF HEPATITIS C VIRUS

(75) Inventor: Philippe Halfon, Marseilles (FR)

(73) Assignee: Panmed Ltd., Beersel (BE)

( * ) Notice: Subject to any disclaimer, the term of this patent is extended or adjusted under 35 U.S.C. 154(b) by 0 days.

(21) Appl. No.: 14/128,684

(22) PCT Filed: Jun. 21, 2012

(86) PCT No.: PCT/IB2012/053143
§ 371 (c)(1),
(2), (4) Date: Dec. 23, 2013

(87) PCT Pub. No.: WO2012/176149
PCT Pub. Date: Dec. 27, 2012

(65) Prior Publication Data
US 2014/0135259 A1 May 15, 2014

Related U.S. Application Data

(60) Provisional application No. 61/500,591, filed on Jun. 23, 2011.

(51) Int. Cl.
A61K 31/4706 (2006.01)
A61K 45/06 (2006.01)
A61K 38/06 (2006.01)
A61K 31/405 (2006.01)

(52) U.S. Cl.
CPC .............. *A61K 45/06* (2013.01); *A61K 31/405* (2013.01); *A61K 31/4706* (2013.01); *A61K 38/06* (2013.01)
USPC .............................. 514/4.3; 514/313; 514/414

(58) Field of Classification Search
None
See application file for complete search history.

(56) References Cited

U.S. PATENT DOCUMENTS

| 5,624,938 A | 4/1997 | Pernis |
| 8,575,195 B2 | 11/2013 | Halfon |
| 2004/0006103 A1 | 1/2004 | Valducci et al. |
| 2005/0009810 A1 | 1/2005 | Savarino |
| 2013/0121965 A1 | 5/2013 | Halfon |

FOREIGN PATENT DOCUMENTS

| WO | WO 2006/109196 | 10/2006 |
| WO | WO 2006/119061 | 11/2006 |
| WO | WO 2007/015855 | 2/2007 |
| WO | WO 2007/016441 | 2/2007 |
| WO | WO 2010/101649 | 9/2010 |
| WO | WO 2011/091757 | 8/2011 |
| WO | WO 2011/161644 | 12/2011 |
| WO | WO 2012/061248 | 5/2012 |
| WO | WO 2012/176149 | 12/2012 |

OTHER PUBLICATIONS

International Preliminary Report on Patentability Dated Jan. 9, 2014 From the International Bureau of WIPO Re. Application No. PCT/IB2012/053143.

Notification of Office Action Dated Jan. 8, 2014 From the State Intellectual Property Office of the People's Republic of China Re. Application No. 201180041185.5 and Its Translation Into English.
Search Report Dated Jan. 8, 2014 From the State Intellectual Property Office of the People's Republic of China Re. Application No. 201180041185.5 and Its Translation Into English.
Communication Pursuant to Article 94(3) EPC Dated Oct. 16, 2013 From the European Patent Office Re. Application No. 11743355.7.
International Preliminary Report on Patentability Dated Jan. 10, 2013 From the International Bureau of WIPO Re. Application No. PCT/IB2011/052762.
International Search Report and the Written Opinion Dated Dec. 7, 2011 From the International Searching Authority Re. Application No. PCT/IB2011/052762.
International Search Report and the Written Opinion Dated Sep. 17, 2012 From the International Searching Authority Re. Application No. PCT/IB2012/053143.
Chandramohan et al. "Preliminary Report of Anti-Hepatitis C Virus Activity of Chloroquine and Hydroxychloroquine in Huh-5-2 Cell Line", Indian Journal of Pharmaceutical Sciences, XP002664360, 68(4): 538-540, Feb. 1, 2006.
Cholongitas et al. "Review Article: Novel Therapeutic Options for Chronic Hepatitis C", Alimentary Pharmacology and Therapeutics, XP002681940, 27(10): 866-884, May 2008. p. 866,879, 874-875.
Freiberg et al. "Combined Chloroquine and Ribavirin Treatment Does Not Prevent Death in a Hamster Model of Nipah and Hendra Virus Infection", Journal of General Virology, 91: 765-772, 2010.

(Continued)

*Primary Examiner* — James D Anderson

(57) ABSTRACT

A combined therapy which utilizes hydroxychloroquine and GNS-227:

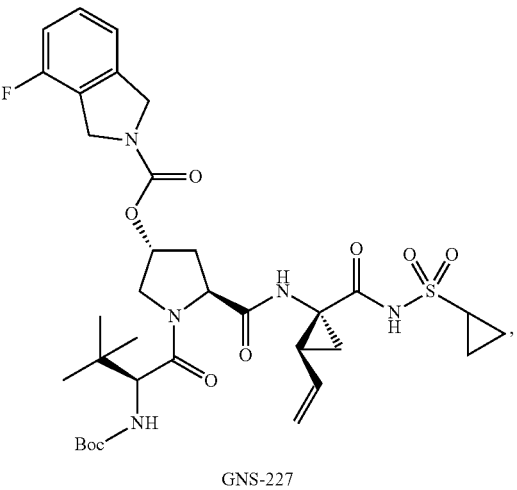

GNS-227 for the treatment of an HCV-related disease, including HCV chronic infection, is disclosed. Further disclosed is pharmaceutical composition (e.g., as a unit dosage form) comprising hydroxychloroquine and GNS-227.

16 Claims, 2 Drawing Sheets
(2 of 2 Drawing Sheet(s) Filed in Color)

(56) References Cited

OTHER PUBLICATIONS

Ge et al. "Autophagy: A Strategy for Malignant Gliomas' Resistance to Therapy", Medical Hypothesis, XP026105246, 73(1): 45-47, Jul. 1, 2009. p. 46, col. 1, Para 3.

Halfon et al. "A New Potent and Selective HCV NS3 Protease Inhibitor With a High Genetic Barrier to Resistance", Journal of Hepatology, XP002681937, 46th Annual Meeting of the European Association for the Study of the Liver (EASL), Berlin, Germany, Mar. 30-Apr. 3, 2011, 54(Suppl.1): S478, Mar. 2011.

Halfon et al. "GNS-227: A New Potent and Selective (2nd Gen) HCV NS3 Protease Inhibitor With a High Genetic Barrier to Resistance", Retrieved from the Internet, XP002681938, 8 P., Mar. 30, 2011.

Kouroumalis et al. "Hydroxychloroquine Reduces Liver Realated Mortality in Hepatitis C Associated (HCV) Compnesated Cirrhosis", GUT, XP009154232, 50(Suppl.2): A114-A115, Abstract #422, Apr. 2002. & Annual Meeting of the British Society of Gastroenterology, Birmingham, England, UK, Mar. 17-20, 2002. Abstract.

Li et al. "Synthesis and SAR of Acyclic HCV NS3 Protease Inhibitors With Novel P4-Benzoxaborole Moieties", Bioorganic & Medicinal Chemistry Letters, XP002681939, 21(7): 2048-2054, Apr. 1, 2011. p. 2051-2052, 2054, Fig.3, Table 2.

Livesy et al. "Autophagy Inhibition in Combination Cancer Treatment", Database Medline [Online], US National Library of Medicine (NLM), XP002664364, Database Accession No. NLM19943199, Dec. 2009. & Current Opinion in Investigational Drugs, 10(12): 1269-1279, Dec. 2009. Abstract.

Malik et al. "A Pilot Study of Hydroxychloroquine in the Treatment of Chronic Hepatitis C", Gastroenterology, XP009154231, 116(4/Pt. 2): A1242-A1243, Abstract #L0274, Apr. 1999. & Digestive Disease Week and the 100th Annual Meeting of the American Gastroeneterological Association, Orlando, FL, USA, May 16-19, 1999. Abstract.

Mizui et al. "Inhibition of Hepatitis C Virus Replication by Chloroquine Targeting Virus-Associated Autophagy", Journal of Gastroenterology, XP019782582, 45(2): 195-203, Sep. 17, 2009. Abstract, p. 198, col. 1, Para 2—p. 201, col. 1, Para 1, Figs.3, 4.

Scola et al. "Discovery and SAR of Tripeptide Acylsulfonamides as Potent Inhibitors of HCV NS3 Protease", Abstracts of Papers American Chemical Society, XP008155035, 238th American Chemical Society National Meeting, Washington, DC, USA Aug. 16-20, 2009, 238: MEDI-229, Aug. 2009.

Wang et al. "Synthesis and SAR of a Series of Potent and Novel Small Molecule Inhibitors of HCV NS3 Protease: Exploring Modified P2 Elements in the Tripeptide Acylsulfonamide Series", Abstracts of Papers American Chemical Society, XP008154980, 238th American Chemical Society National Meeting, Washington, DC, USA, Aug. 16-20, 2009, 238: MEDI-106, Aug. 2009.

Zuckerman et al. "Management of Hepatitis C Virus-Related Arthritis", BioDrugs: Clinical Immunotherapeutics, Biopharmaceuticals and Gene Therapy, XP009154221, 15(9): 573-584, 2001. Abstract, p. 581, col. 2, Para 3, Fig.2.

Official Action Dated Apr. 25, 2014 From the US Patent and Trademark Office Re. U.S. Appl. No. 13/726,783.

TREATMENT OF HEPATITIS C VIRUS

RELATED APPLICATIONS

This application is a National Phase of PCT Patent Application No. PCT/IB2012/053143 having International filing date of Jun. 21, 2012, which claims the benefit of priority under 35 USC §119(e) of U.S. Provisional Patent Application No. 61/500,591 filed on Jun. 23, 2011. The contents of the above applications are all incorporated by reference as if fully set forth herein in their entirety.

FIELD AND BACKGROUND OF THE INVENTION

The present invention, in some embodiments thereof, relates to therapy and, more particularly, but not exclusively, to a novel methodology for the treatment of hepatitis C virus (HCV) related diseases.

Infection by hepatitis C virus (HCV) is a compelling human medical problem. HCV is recognized as the causative agent for most cases of non-A, non-B hepatitis, with an estimated human sero-prevalence of 3% globally. Nearly four million individuals may be infected in the United States alone. Upon first exposure to HCV only about 20% of infected individuals develop acute clinical hepatitis while others appear to resolve the infection spontaneously. In almost 70% of instances, however, the virus establishes a chronic infection that persists for decades. This usually results in recurrent and progressively worsening liver inflammation, which often leads to more severe disease states such as cirrhosis and hepatocellular carcinoma.

The combination of a pegylated interferon (e.g., peg-IFN alpha-2a/b) and twice-daily oral doses of ribavirin, an antiviral agent, is the current standard of care for the treatment of chronic HCV infection. Patients who will ultimately achieve a sustained virologic response to peg-IFN and ribavirin therapy usually develop a rapid decline in HCV-RNA levels after initiation of therapy, with levels becoming undetectable within 4-24 weeks. Liver enzyme levels become normal, and histologic findings improve markedly. With the above-mentioned combination therapy, approximately 75% to 80% of patients with HCV genotype 2 or 3 infection and 40% to 50% of those with genotype 1 infection achieve a sustained virologic response (SVR) [Sherman K. E., Clinical Need and Therapeutic Targets for New HCV Agents, in The Future of HCV: Small molecules in Development for Chronic Hepatitis C, Clinical Care Options LLC, 2007].

However, success rate of this combined therapy is limited as its outcome is highly dependent on the infecting HCV genotype. This treatment is effective in fewer than 50% of patients infected with HCV genotype 1 or 4, the most represented genotypes in Europe and USA. In many cases, non-response is related to host or viral factors that impair activation of the host's innate, interferon-driven immune response.

Others may achieve viral reduction during therapy but cannot tolerate full therapeutic doses or an adequate duration of treatment because of cytopenia, fatigue, or other adverse effects of treatment. Indeed, dose modifications for these reasons are required in 35% to 42% of treated patients, and approximately one third of these patients eventually discontinue treatment altogether. These dose reductions, temporary interruptions, and aborted treatment courses reduce the chance of achieving SVR.

Finally, the combination of peg-IFN and ribavirin is contraindicated altogether in many patients who are in need of anti-HCV therapy. Contraindications for therapy include severe cytopenia, hepatic decompensation, renal insufficiency, poorly controlled autoimmune disease, severe cardiopulmonary disease, and active psychological problems. [Davis G. L., Investigational Small-Molecule Agents for the Treatment of Chronic Hepatitis C, in The Future of HCV: Small molecules in Development for Chronic Hepatitis C, Clinical Care Options LLC, 2007].

Alternative therapies for the treatment of HCV related diseases have been developed. Such therapies are disclosed, for example, in U.S. Pat. Nos. 6,849,254; 7,115,578; 7,410,979; 7,671,017 discloses the use of cyclosporine and pegylated interferon for treating HCV.

One of the current approaches for treating HCV utilizes HCV protease inhibitors. See, for example, Chen K X, Njoroge F G. A review of HCV protease inhibitors. *Curr Opin Investig Drugs*. 2009 8, 821-37; 2: Garg G, Kar P. Management of HCV infection: current issues and future options. *Trop Gastroenterol*. 2009 30, 11-8; 3: Pereira A A, Jacobson I M. New and experimental therapies for HCV. *Nat Rev Gastroenterol Hepatol*. 2009 7, 403-11.

HCV is a positive-stranded RNA virus which has been classified as a separate genus in the Flaviviridae family. All members of the Flaviviridae family have enveloped virions that contain a positive stranded RNA genome encoding all known virus-specific proteins via translation of a single, uninterrupted, open reading frame. The single strand HCV RNA genome is approximately 9500 nucleotides in length and has a single open reading frame (ORF) encoding a single large polyprotein of about 3,000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The NS3 protein also exhibits nucleoside triphosphatase and RNA helicase activities. NS5B is a RNA-dependent RNA polymerase that is involved in the replication of HCV.

The NS3 serine protease, located in the N-terminal domain of the NS3 protein, mediates all of the subsequent cleavage events downstream in the polyprotein. Because of its role, the NS3 serine protease is an ideal drug target. Hexapeptides as well as tripeptides show varying degrees of inhibition of NS3 serine protease are described, for example, in U.S. patent applications having publication Nos. U.S. 2005/0020503, U.S. 2004/0229818, and U.S. 2004/00229776. Macrocyclic compounds that exhibit anti-HCV activity have been disclosed, for example, in WO 20061119061, WO 2007/015855 and WO 2007/016441 (all by Merck & Co., Inc.).

The discovery of novel antiviral strategies to selectively inhibit HCV replication has long been hindered by the lack of convenient cell culture models for the propagation of HCV. This hurdle has been overcome first with the establishment of the HCV replicon system in 1999 (Bartenschlager, R., *Nat. Rev. Drug Discov.* 2002, 1, 911-916 and Bartenschlager, R., *J. Hepatol*. 2005, 43, 210-216) and, in 2005, with the development of robust HCV cell culture models (Wakita, T., et al., Nat. Med. 2005, 11, 791-6; Zhong, J., et al., Proc. Natl. Acad. Sci. U.S.A. 2005, 102, 9294-9; Lindenbach, B. D., et al., Science 2005, 309, 623-6).

Chloroquine is a well known lysosomotropic agent, currently attracting many hopes in terms of antiviral therapy as well as in antitumoral effect because of its pH-dependent inhibiting action on the degradation of cargo delivered to the lysosome, thus effectively disabling this final step of the autophagy pathway.

Hydroxychloroquine (HCQ) is a chemical derivative of chloroquine (CQ) which features a hydroxyethyl group instead of an ethyl group.

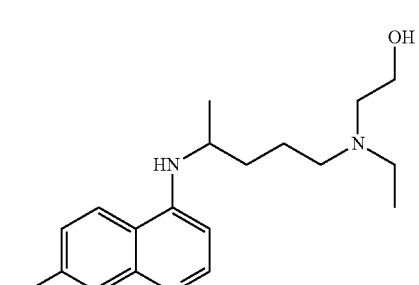

Hydroxychloroquine
(RS)-2-[{4-[7-chloroquinolin-4-Hyl)amino]pentyl}(ethyl)amino]ethanol

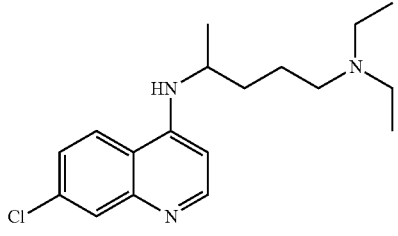

Chloroquine
N'-(7-chloroquinolin-4-yl)-N,N-diethyl-pentane-1,4-diamine

HCQ has been classified as an effective anti-malarial medication, and has shown efficacy in treating systemic lupus erythematosus as well as rheumatoid arthritis and Sjögren's Syndrome. While HCQ has been known for some time to increase lysosomal pH in antigen presenting cells, its mechanism of action in inflammatory conditions has been only recently elucidated and involves blocking the activation of toll-like receptors on plasmacytoid dendritic cells (PDCs).

A direct comparison of the therapeutic effect of CQ and HCQ is quite difficult but it has been suggested that hydroxychloroquine was one-half to two-thirds as effective as chloroquine in treating rheumatologic diseases and one-half as toxic [Scherbel A L et al., Cleve Clin Q, 1958, 25:95]. Since chloroquine appears to be much more retinotoxic frequent use of hydroxychloroquine is increasing [Rynes R. I., British Journal of Rheumatology, 1997; 36:799-805].

Chloroquine and derivatives thereof such as HCQ have been discussed in the context of HCV therapy in, for example, Chandramohan M. et al. [Indian J Pharm Sci 2006; 68:538-40]; Freiberg et al. [Journal of General Virology (2010), 91, 765-772]; Zuckerman et al. [BioDrugs 2001; 15(9), pp. 574-584]; Mizui et al. [J. Gastroenterol. 2010 February; 45(2): 195-203. Epub 2009 Sep. 17].

Additional background art includes WO 2012/061248 and WO 2011/161644.

SUMMARY OF THE INVENTION

According to an aspect of some embodiments of the present invention there is provided a method of treating a hepatitis C virus (HCV) related disease in a subject in need thereof, the method comprising co-administering to the subject a therapeutically effective amount of hydroxychloroquine or a pharmaceutically acceptable salt thereof in combination with a therapeutically effective amount of the compound GNS-227:

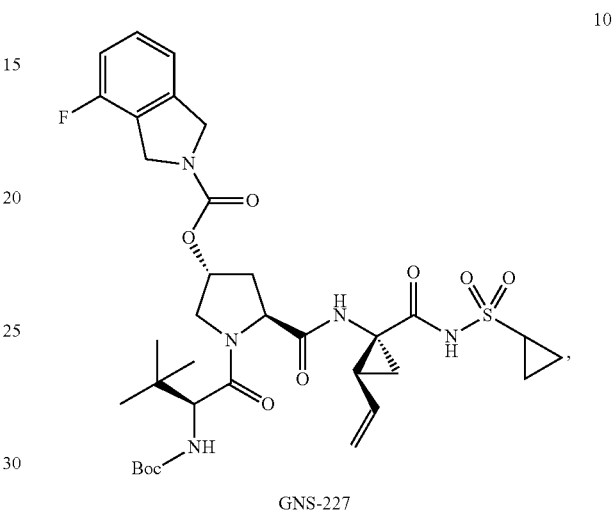

GNS-227 thereby treating the HCV related disease.

According to an aspect of some embodiments of the present invention there is provided a use of a therapeutically effective amount of hydroxychloroquine or a pharmaceutically acceptable salt thereof in the manufacture of a medicament for treating a hepatitis C virus (HCV) related disease in a subject in need thereof, the medicament being identified for use in combination with a therapeutically effective amount of the compound GNS-227.

According to an aspect of some embodiments of the present invention there is provided a hydroxychloroquine or a pharmaceutically acceptable salt thereof for use in the treatment of a hepatitis C virus (HCV) related disease in a subject in need thereof, wherein a therapeutically effective amount of the hydroxychloroquine or the pharmaceutically acceptable salt thereof is used in combination with a therapeutically effective amount of the compound GNS-227.

According to some embodiments of the invention, the therapeutically effective amount of hydroxychloroquine and the therapeutically effective amount of the GNS-227 are selected such that hydroxychloroquine and the GNS-227 act in synergy.

According to some embodiments of the invention, the therapeutically effective amount of hydroxychloroquine is in a range of from 100 to 2000 mg per day.

According to some embodiments of the invention, the therapeutically effective amount of hydroxychloroquine is in a range of from 800 to 1000 mg per day.

According to some embodiments of the invention, the HCV related disease is a chronic HCV infection.

According to some embodiments of the invention, the HCA related disease is caused by an anti-viral resistant genotype of the HCV.

According to some embodiments of the invention, the method further comprises co-administering to the subject of a therapeutically effective amount of an additional antiviral agent.

According to an aspect of some embodiments of the present invention there is provided a pharmaceutical composition comprising hydroxychloroquine or a pharmaceutically acceptable salt thereof, a compound GNS-227 and a pharmaceutically acceptable carrier.

According to some embodiments of the invention, the composition is identified for use in the treatment of a hepatitis C virus (HCV) related disease.

According to some embodiments of the invention, the composition is formulated for oral administration.

According to some embodiments of the invention, the composition is in a solid form.

According to some embodiments of the invention, the composition is a unit dosage form of the composition.

According to an aspect of some embodiments of the present invention there is provided a pharmaceutical composition unit dosage form comprising hydroxychloroquine or a pharmaceutically acceptable salt thereof, the compound GNS-227 and a pharmaceutically acceptable carrier.

According to some embodiments of the invention, the composition is identified for use in the treatment of a hepatitis C virus (HCV) related disease.

According to some embodiments of the invention, the composition is formulated for oral administration.

According to some embodiments of the invention, the composition is in a solid form.

According to some embodiments of the invention, an amount of hydroxychloroquine and an amount of the GNS-227 are selected such that the hydroxychloroquine and the GNS-227 act in synergy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
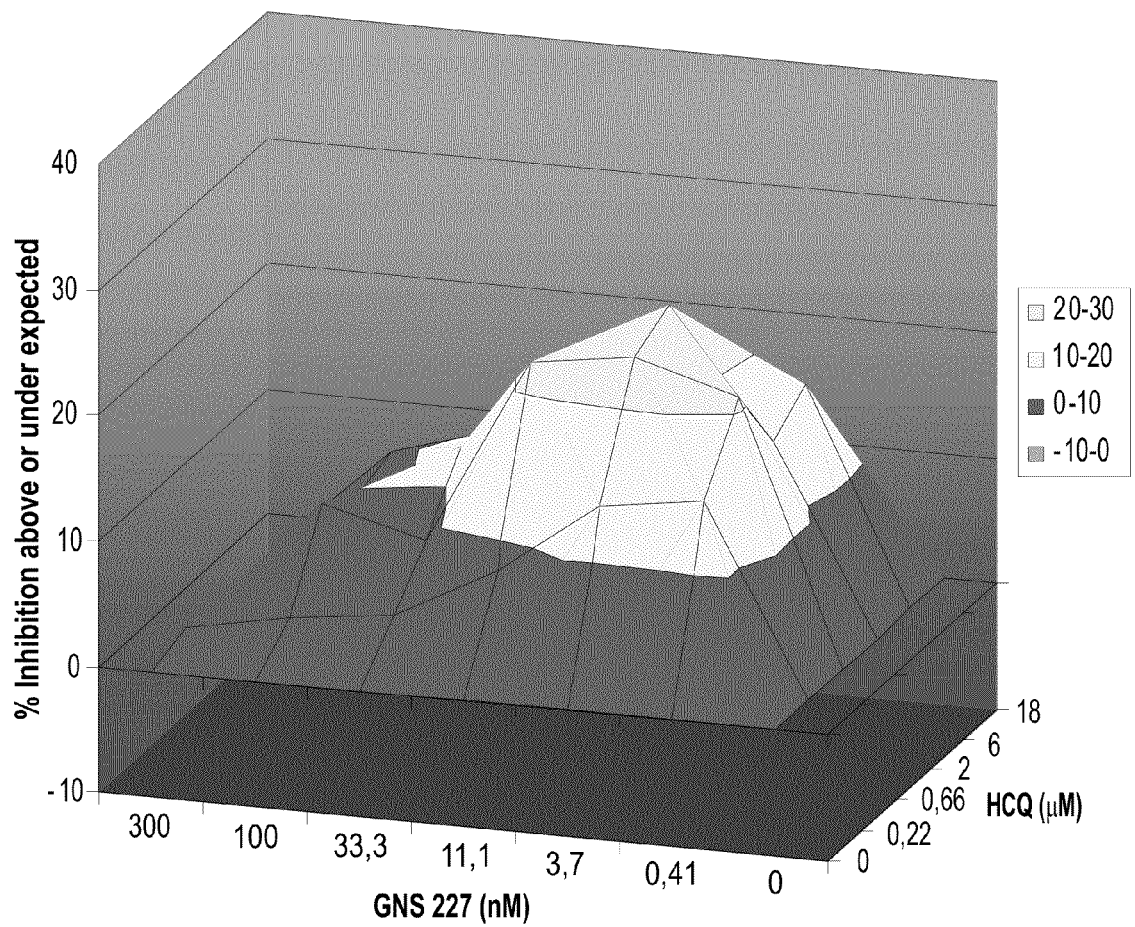

FIG. 1 presents the data obtained for the anti-viral effect of the combination of GNS-227 with hydroxychloroquine in short-term (3 days) antiviral assay, as analyzed using the Prichard and Shipman. The different colors represent different ranges of values: burgundy: 0 to 10%; yellow: 10 to 20% and blue: 20 to 30%. The 0 plane on the Z-axis represents an additive effect. A surface that is higher than 20% above the zero plane indicates a synergistic effect of the combination, a surface lower than 20% below the zero plane indicates antagonism between the drugs.

Figure 2:
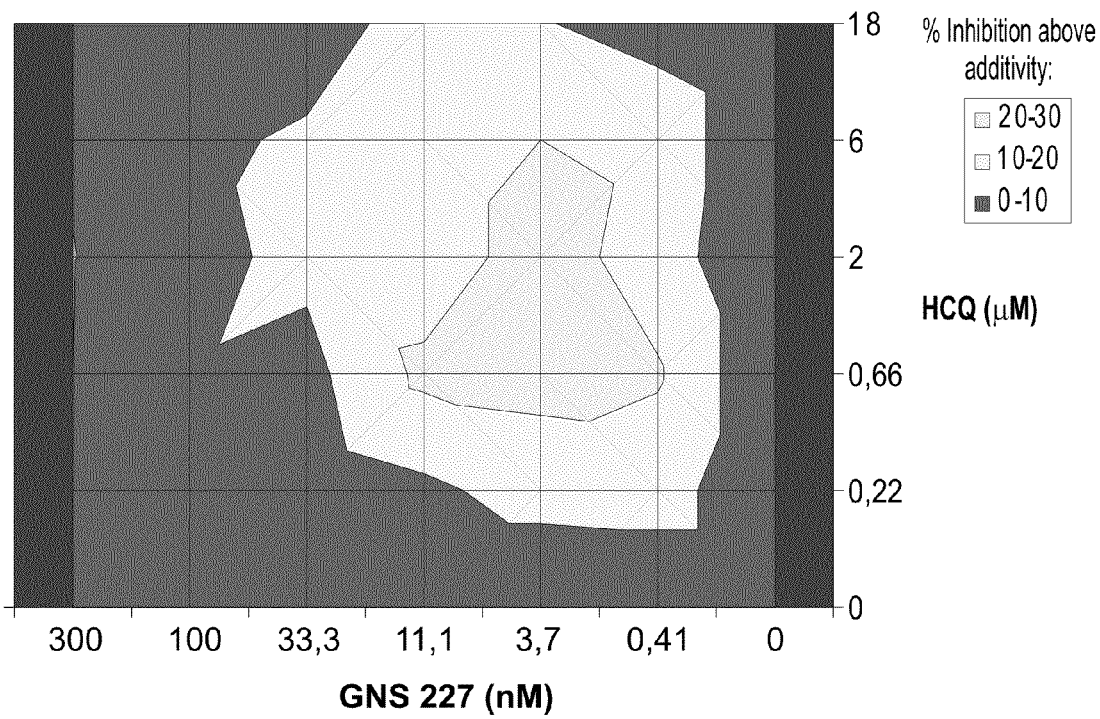

FIG. 2 presents a two-dimensional representation of the antiviral effect of the combination of GNS-227 and hydroxychloroquine as determined by Bliss independence modeling of variable drug ratio combinations. The values associated with synergy (positive numbers) and antagonism (negative numbers) are indicated.

Figure 3:
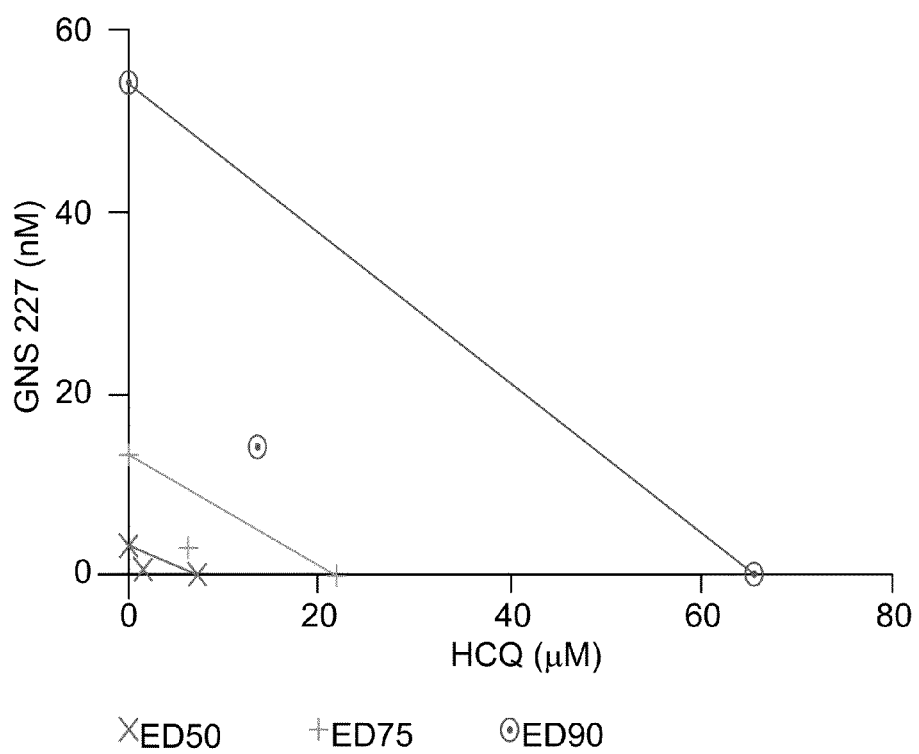

FIG. 3 presents an isobologram analysis of the data obtained for antiviral effect of the combination of GNS-227 and hydroxychloroquine analysed by using Calcusyn program and shown as a traditional isobologram, in which the lines represent the EDs of the two drugs required to achieve 50, 75, or 90% inhibition if the effects of the two compounds were simply additive. The dots are the actual experimental doses used to achieve those effects.

DESCRIPTION OF SPECIFIC EMBODIMENTS OF THE INVENTION

The present invention, in some embodiments thereof, relates to therapy and, more particularly, but not exclusively, to a novel methodology for the treatment of hepatitis C virus (HCV) related diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for a novel methodology for treating HCV related diseases, and chronic HCV infection in particular, which would obviate the non-responsiveness and/or non-tolerance associated with the current methodologies, the present inventors have surprisingly uncovered that a combination of HCQ and the compound GNS-227:

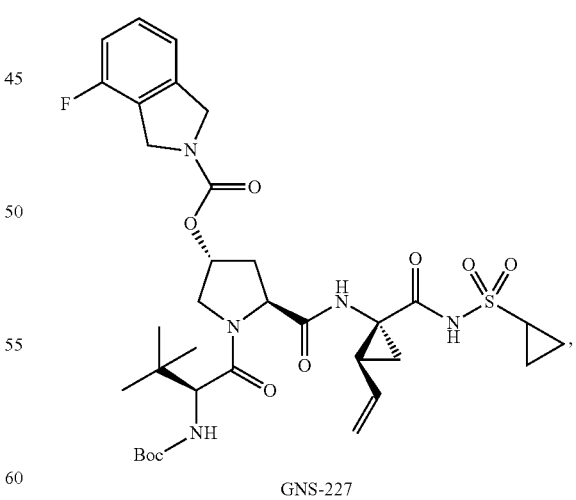

GNS-227 can be efficiently used as a therapy for treating HCV related diseases, as defined herein.

HCQ has been previously suggested as an agent for treating HCV. GNS-227 is shown herein to exhibit a protease inhibition activity as well as an antiviral activity towards HCV.

As demonstrated in the Examples section that follows, the present inventors have shown that HCQ and GNS-227 may act in synergy, thus providing for an improved therapeutic effect of these agents.

Thus, it is demonstrated herein that exemplary combinations of HCQ and GNS-227 exhibit at least an additive effect, and even a synergistic effect, as determined by various theoretical models (see, FIGS. 1-3 and Table 1). As shown in FIGS. 1-3, none of the tested combinations exhibited an antagonistic effect.

It has been shown that synergy was achieved when cells were treated with HCQ at a concentration of from about 0.66 µM about 6 µM and was best achieved when cells were treated with HCQ at a concentration of about 6 µM. This dose can be translated, using recognized conversion factors, into a dose of about 910 mg for an average human weighing 70 Kg.

It has further been shown that synergy was best achieved when cells were treated with GNS-227 at a concentration of from about 0.37 nM to about 11.1 µM, and was best achieved when cells were treated with GNS-227 at a concentration of about 3.7 nM. This dose can be translated, using recognized conversion factors, into a dose of about 10 mg for an average human weighing 70 Kg.

The above-described findings suggest that treatment of an HCV related disease such as an HCV infection can be beneficially effected while utilizing HCQ in combination with GNS-227.

It is noted that HCQ is known as a less toxic derivative of chloroquine. Thus, higher doses of HCQ can be tolerable, compared to chloroquine.

According to an aspect of some embodiments of the present invention there is provided a method of treating a hepatitis C virus (HCV) related disease in a subject in need thereof. The method is effected by administering to the subject a therapeutically effective amount of hydroxychloroquine (HCQ) or a pharmaceutically acceptable salt thereof, and a therapeutically effective amount of GNS-227, thereby treating the HCV related disease.

According to an aspect of some embodiments of the present invention there is provided a use of a therapeutically effective amount of hydroxychloroquine (HCQ) or a pharmaceutically acceptable salt thereof in the manufacture of a medicament for treating a hepatitis C virus (HCV) related disease in a subject in need thereof, the medicament being for use in combination with and a therapeutically effective amount of GNS-227.

According to an aspect of some embodiments of the present invention there is provided a hydroxychloroquine (HCQ) or a pharmaceutically acceptable salt for use in the treatment of a hepatitis C virus (HCV) related disease in a subject in need thereof, wherein a therapeutically effective amount of HCQ or the salt thereof is used in combination with and a therapeutically effective amount of GNS-227.

As used herein throughout, the term "hepatitis C virus", abbreviated HCV, describes an enveloped, positive-sense single-stranded RNA virus of the family Flaviviridae, which is the cause of hepatitis C in humans, and encompasses all genotypes of the virus, unless otherwise indicated.

Currently known HCV genotypes include genotypes 1, 2, 3, 4, 5 and 6, of which genotypes 1 and 4 are relatively non-responsive to existing treatments (e.g., interferon and ribavirin), whereas genotypes 2, 3, 5 and 6 are more responsive to treatment.

In some embodiments, the HCV related disease is an infection caused by HCV, including all genotypes of HCV, as defined herein.

In some embodiments, the infection caused by HCV is an acute infection, encompassing any acute phase of an HCV infection (e.g., the first 6 months after infection), also termed herein and in the art "acute HCV infection".

An "acute HCV infection" thus relates to an infection which has been eliminated, namely, to cases where viral replication has been eliminated and the virus is eradicated.

If viral replication is not successfully inhibited within the acute phase, the HCV infection is considered a chronic infection.

In some embodiments, the infection caused by HCV is a chronic infection, also termed herein and in the art "chronic HCV infection".

As used herein throughout, the phrase "HCV related disease" also encompasses any disease or disorder associated with an HCV infection, including symptoms associated with an acute HCV infection, such as decreased appetite, fatigue, abdominal pain, jaundice, itching and flu-like symptoms, as well as symptoms associated with a chronic HCV infection, such as fatigue, flu-like symptoms, joint pains, arthritis, polyarthralgia, cutaneous leukocytoclastic vasculatis, neuropathy, itching, sleep disturbances, appetite changes, nausea, depression, liver cirrhosis, ascites, a tendency toeards bruising and/or bleeding, varices, jaundice, hepatic encephalopathy, porphyria cutanea cardia, cryoglobulinemia, glomerulonephritis (e.g., membranoproliferative glomerulonephritis), thrombocytopenia, lichen planus, diabetes mellitus, and lymphoproliferative disorders.

Some types of HCV related disease are inflammatory conditions (e.g., arthritis) which may be treated by a relatively simple anti-inflammatory therapy. However, other types of HCV related disease may be more difficult to treat.

In some embodiments, the phrase "HCV related disease" refers to an HCV disease other than such inflammatory conditions (e.g., other than arthritis).

In addition, disease caused by an HCV genotype resistant to an antiviral agent (antiviral-resistant) may be particularly difficult to treat successfully.

Currently known resistant HCV genotypes include genotype 1 HCV and genotype 4 HCV. These genotypes are known in the art to exhibit resistance to antiviral agents commonly used to treat HCV related disease.

In some embodiments, the HCV related disease is caused by an antiviral-resistant HCV genotype.

Resistance can be inherent to an organism or acquired (e.g., as a result of exposure to an antiviral agent resulting in selection for a mutant genotype resistant to the agent). When resistance is acquired upon exposure to an antiviral agent, the resistance may be specific to that antiviral agent (and in some cases highly similar antiviral agents), or the acquired resistance may to a variety of antiviral agents, including antiviral agents to which the organism was not exposed.

As used herein, a "subject" describes any mammal afflicted, or suspected as being afflicted, by an HCV related disease as described herein, and/or to whom the treatment methods described herein are desired, including human, bovine, equine, canine, murine and feline subjects. In some embodiments, the subject is a human.

In some embodiments, "a subject in need thereof" is a subject diagnosed as having an HCV-related disease. Determining an HCV-related disease can be made by blood tests for detecting antibodies to HCV, and molecular nucleic acid tests for detecting the presence of HCV (e.g., polymerase, chain reaction, transcription mediated amplification and/or branched DNA methods). Optionally, both antibody and nucleic acid tests are used, in order to confirm that an HCV infection is present. The particular HCV-related disease can be determined by a physician using standard methods (e.g., physical examination, liver function tests), depending on which symptoms are present in a subject.

In some embodiments "a subject in need thereof" is a subject who is afflicted by an HCV-related disease, such as chronic HCV infection, and who was treated with an anti-viral agent or a combination of anti-viral agents, but was identified as non-responsive to the treatment or as non-tolerant to the treatment.

As used herein, the term "non-responsive" refers to a failure of an antiviral therapy used in the art against HCV (e.g., a treatment with PEGylated interferon-α-2a or PEGylated interferon-α-2b, in combination with ribavirin), and optionally a failure of two such antiviral therapies, to abrogate, substantially inhibit, slow or reverse the progression of an HCV-related disease, or substantially ameliorateing clinical symptoms of an HCV-related disease.

In some embodiments, non-responsiveness to treatment is a result of an HCV (e.g., an HCV genotype) which is resistant to the therapy. Alternatively or additionally, non-responsiveness is due to the subject (e.g., physiology of the subject, poor compliance by the subject). In some embodiments, the reason(s) for non-responsiveness are not known.

As used herein, the term "non-tolerant" refers to the development of one or more adverse effects in a treated subject, which are judged by a physician to be due to the treatment, wherein the adverse effects are sufficiently severe such as to require ending or altering the treatment (e.g., by reducing the dosage of the anti-viral therapy and/or by replacing the anti-viral therapy).

As used herein, the term "hydroxychloroquine" includes the racemic hydroxychloroquine, which is 2-[[4-[(7-chloro-4-quinolinyl)amino]pentyl]ethylamino]ethanol as disclosed in U.S. Pat. No. 2,546,658, or any of the single enantiomers "(S)-(+) hydroxychloroquine" or "(R)-(+) hydroxychloroquine" as disclosed in U.S. Pat. No. 5,314,894. This term may relate either to the free form of hydroxychloroquine or to any pharmaceutically acceptable salt thereof, such as hydroxychloroquine sulfate.

It is noted that in any of the methods and uses described herein, chloroquine or chloroquine derivatives other than HCQ are also contemplated.

Herein, the term "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. Examples, without limitation, of pharmaceutically acceptable salts include salts comprising an anion such as a carboxylate or sulfate anion, and/or a cation such as, but not limited to, ammonium, sodium, potassium and the like. Suitable salts are described in, e.g., Birge et al. [J Pharm Sci 1977, 66:1-19]. An example of pharmaceutically acceptable salt of hydroxychloroquine is hydroxychloroquine sulfate.

Hydroxychloroquine (HCQ) is currently used in treatments of malaria, lupus erythematosus, rheumatoid arthritis, post-Lyme disease arthritis, and Sjogren's syndrome, typically at a daily dose of 200 mg or 400 mg.

Due to its lower toxicity compared to chloroquine, high peak levels of HCQ are considered to be tolerable.

As used herein, the term "therapeutically effective amount" describes an amount of a compound described herein which upon being administered will relieve to some extent one or more of the symptoms of the condition being treated.

In the context of some embodiments of the present invention, a "therapeutically effective amount" describes an amount which eradicates or reduces HCV replication. Such an amount can also be defined herein as an amount that prevents an acute HCV infection from turning into a chronic HCV infection.

In some embodiments, the therapeutically effective amount of each of the HCQ and the GNS-227 as described herein are selected such that the compounds act in synergy.

By "synergy" it is meant that the effect of the compounds when administered in combination is greater than an additive effect of the compounds when administered alone as a single agent.

As exemplified in the Examples below, synergy can be determined according to methods described, for example, by Prichard & Shipman [*Antiviral Res* 1990, 14:181-205], wherein the theoretical additive effect is calculated from dose-response curves of individual compounds by the equation $Z=X+Y(1-X)$, where X and Y represent the inhibition produced by the individual compounds and Z represents the effect produced by the combination of compounds. An effect of a combination of compounds which is higher than Z (optionally 20% higher, and optionally 30% higher) indicates synergism.

As further exemplified in the Examples below, synergy can be determined according to methods described by Chou & Talalay [*Trends Pharmacol Sci* 1983, 4:450-454; *Adv Enzyme Regul* 1984, 22:27] and/or using an isobologram, e.g., as described by Tallarida [*J Pharmacol Exp Therap* 2001, 298: 865-872].

In some embodiments, a synergistic effect is determined according to the abovementioned method of Prichard & Shipman. In exemplary some embodiments, a synergistic effect is determined according to each of the abovementioned methods.

Combinations which act in synergy are also referred to herein as synergistic combinations.

Therapeutically effective amounts which result in synergy may be selected by determining the effects of different combinations of HCQ and the GNS-227 (optionally including the effects of HCQ alone and/or the GNS-227 alone), as exemplified in the Examples section.

In some embodiments, synergy is effected using an amount of HCQ which is at least 400 mg per day (e.g., in a range of from 400 to 2000 mg per day), preferably at least 500 mg per day (e.g., from 500 to 1000 mg per day), optionally at least 600 mg per day, and optionally at least 800 mg per day (e.g., 800-1000 mg/day, 850-950 mg/day, 900 mg/day). Suitable ranges of at least 600 mg per day and at least 800 mg per day are described elsewhere herein.

In some embodiments, the therapeutically effective amount of HCQ or a salt thereof ranges between 100 mg to 2000 mg per day, including any integer within this range.

In some embodiments, the therapeutically effective amount of HCQ or a salt thereof is 100 mg per day.

In some embodiments, the therapeutically effective amount of HCQ or a salt thereof is 200 mg per day.

In some embodiments, the therapeutically effective amount of HCQ or a salt thereof is 300 mg per day.

In some embodiments, the therapeutically effective amount of HCQ or a salt thereof is 400 mg per day.

In some embodiments, the therapeutically effective amount of HCQ or a salt thereof is 500 mg per day.

In some embodiments, the therapeutically effective amount of HCQ or a salt thereof is 600 mg per day.

In some embodiments, the therapeutically effective amount of HCQ or a salt thereof is 700 mg per day.

In some embodiments, the therapeutically effective amount of HCQ or a salt thereof is 800 mg per day.

In some embodiments, the therapeutically effective amount of HCQ or a salt thereof is 900 mg per day.

In some embodiments, the therapeutically effective amount of HCQ or a salt thereof is 1000 mg per day.

In some embodiments, the therapeutically effective amount of HCQ or a salt thereof is 1100 mg per day.

In some embodiments, the therapeutically effective amount of HCQ or a salt thereof is 1200 mg per day.

In some embodiments, the therapeutically effective amount of HCQ or a salt thereof is 1300 mg per day.

In some embodiments, the therapeutically effective amount of HCQ or a salt thereof is 1400 mg per day.

In some embodiments, the therapeutically effective amount of HCQ or a salt thereof is 1500 mg per day.

In some embodiments, the therapeutically effective amount of HCQ or a salt thereof is 1600 mg per day.

In some embodiments, the therapeutically effective amount of HCQ or a salt thereof is 1700 mg per day.

In some embodiments, the therapeutically effective amount of HCQ or a salt thereof is 1800 mg per day.

In some embodiments, the therapeutically effective amount of HCQ or a salt thereof is 1900 mg per day.

In some embodiments, the therapeutically effective amount of HCQ or a salt thereof is 2000 mg per day.

In some embodiments, the amount of HCQ utilized in the various aspects of embodiments of the present invention is higher than the amount of HCQ required to exert currently known therapeutic effects, including the amount known to date to be therapeutically effective in the treatment of malaria, lupus erythematosus, rheumatoid arthritis, post-Lyme disease arthritis and Sjogren's syndrome, and including an amount considered effective for treating HCV infections.

In some embodiments, the amount of HCQ is higher than the amount of HCQ required to exert currently known therapeutic effects by at least 10%, and can be, for example, higher by from 10% to about 50% or from about 10% to about 100% or even 200%.

In some embodiments, the amount of HCQ is at least 400 mg per day.

In some embodiments, the amount of HCQ is at least 500 mg per day.

In some embodiments, the amount of HCQ is at least 600 mg per day.

In some embodiments, the amount of HCQ is at least 700 mg per day.

In some embodiments, the amount of HCQ is at least 800 mg per day.

In some embodiments, the amount of HCQ is at least 900 mg per day.

In some embodiments, the amount of HCQ is at least 1000 mg per day.

In some embodiments, the amount of HCQ ranges from 500 mg to 1500 mg per day.

In some embodiments, the amount of HCQ ranges from 600 mg to 1200 mg per day.

In some embodiments, the amount of HCQ ranges from 800 mg to 1200 mg per day.

In some embodiments, the amount of HCQ ranges from 600 mg to 1000 mg per day.

In some embodiments, the amount of HCQ ranges from 800 mg to 1000 mg per day.

In some embodiments, the amount of HCQ ranges from 900 mg to 1100 mg per day.

In some embodiments, the amount of HCQ ranges from 850 mg to 950 mg per day.

Any integer between the above-indicated ranges is contemplated.

Herein throughout, whenever an amount of HCQ is indicated, it encompasses the same amount of an HCQ pharmaceutically acceptable salt as described herein, or an equimolar amount of an HCQ pharmaceutically acceptable salt.

Similarly, whenever an amount of HCQ is indicated, it encompasses the same amount of chloroquine or another chloroquine derivative, as described herein, or an equimolar amount of chloroquine or the additional chloroquine derivative.

Herein throughout, whenever an amount of HCQ or of a salt thereof is indicated as an amount per day, it can be administered once, twice, thrice and even four-times a day.

In some embodiments, the method is effected by administering a therapeutically effective amount of HCQ or a salt thereof once a day.

When administered more than once a day (e.g., twice or thrice a day), the above-indicated amounts are divided to the respective administration times.

For example, in embodiments in which the method is effected by administering an amount of HCQ which is 900 mg per day, and comprises 2 daily administrations, 450 mg of HCQ are used in each administration. Alternatively, one administration is of 400 mg and another is of 500 mg. If such a daily dosage is to be administered 3 times a day, 300 mg of HCQ can be used, as an example, in each administration.

In embodiments in which the method is effected by administering an amount of HCQ which is 600 mg per day, 300 mg of HCQ are used in each of two daily administrations. Alternatively, one administration is of 200 mg and another is of 400 mg. Alternatively, 200 mg of HCQ are used in each of three daily administrations.

In embodiments in which the method is effected by administering an amount of HCQ which is 800 mg per day, and comprises 2 daily administrations, 400 mg of HCQ are used in each administration. Alternatively, one administration is of 200 mg and another is of 600 mg. Alternatively, 200 mg of HCQ are used in each of four daily administrations.

In embodiments in which the method is effected by administering an amount of HCQ which is 1000 mg per day, and comprises 2 daily administrations, 500 mg of HCQ are used in each administration. Alternatively, one administration is of 400 mg and another is of 600 mg. Alternatively, the method comprises 3 daily administrations, for example, two of 400 mg and one of 200 mg. Alternatively, the method comprises 4 daily administrations, for example, wherein each administration is of 250 mg.

In some embodiments, the therapeutically effective amount of GNS-227 or a salt thereof ranges from 1 mg to 1000 mg per day, including any integer within this range. Higher amounts are also contemplated.

In some embodiments, the amount of GNS-227 or a salt thereof ranges from 1 mg to 50 mg per day.

In some embodiments, the amount of GNS-227 or a salt thereof ranges from 5 mg to 50 mg per day.

In some embodiments, the amount of GNS-227 or a salt thereof ranges from 5 mg to 20 mg per day.

In some embodiments, the amount of GNS-227 or a salt thereof ranges from 5 mg to 15 mg per day.

In some embodiments, the amount of GNS-227 or a salt thereof ranges from 8 mg to 12 mg per day.

In some embodiments, the amount of GNS-227 or a salt thereof is about 10 mg per day.

Any integer between the above-indicated ranges is contemplated.

Herein throughout, whenever an amount of GNS-227 is indicated, it encompasses the same amount of a GNS-227 pharmaceutically acceptable salt as described herein, or an equimolar amount of a GNS-227 pharmaceutically acceptable salt.

Herein throughout, whenever an amount of GNS-227 or of a salt thereof is indicated as an amount per day, it can be administered once, twice, thrice and even four-times a day.

In some embodiments, the method is effected by administering a therapeutically effective amount of GNS-227 or a salt thereof once a day.

When administered more than once a day (e.g., twice or thrice a day), the above-indicated amounts are divided to the respective administration times.

A salt of GNS-227 is preferably a pharmaceutically acceptable salt, as defined herein, such as, for example, as acid addition salt.

The HCQ, GNS-227 or any of the other agents described herein can also be utilized in a form of a prodrug, solvate or hydrate thereof.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo.

The term "solvate" refers to a complex of variable stoichiometry (e.g., di-, tri-, tetra-, penta-, hexa-, and so on), which is formed by a solute (the compound of present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The amount of the prodrug, hydrate or solvate can be calculated so as to be an equimolar amount of the agents, as described herein.

GNS-227, as presented herein, has chiral atoms, each being of a specific configuration. It is to be understood that other enantiomers, diastereomers, and any racemic mixtures thereof are also contemplated and are encompassed by the expression "GNS-227", such that each chiral carbon atom in the molecule can posses an R or S configuration or can be a racemic mixture.

Also encompassed are any isomorphs of GNS-227.

As used herein, the term "co-administering" describes administering to the subject the two agents, HCQ and GNS-227, as defined herein, during the treatment. This term encompasses administering the GNS-227 prior to, concomitant with or subsequent to administering the HCQ or the salt thereof. This term also encompasses administering the two agents via the same route of administration or via different routes of administration. This term further encompasses administering the two agents within a single pharmaceutical composition or in two separate pharmaceutical compositions, each comprising a single agent, as is further detailed hereinbelow.

The phrase "for use in combination with" means that the agents or medicaments comprising the agents are co-administered, as defined herein.

In some embodiments, co-administering is effected such that the efficacy window of the HCQ and the efficacy window of the GNS-227 substantially overlap.

As is well known in the art, an efficacy window of an agent depends on various factors such as systemic absorbance rate, the time required to reach a plasma peak concentration and/or clearance rate.

It is often desirable to treat subjects suffering from an HCV-related disease with two or more compounds which exhibit an antiviral effect, so as to simultaneously act on the virus via two or more antiviral mechanisms, particularly when the compounds act in synergy.

Simultaneous action of two or more agents can be achieved if the agents exhibit their effect within the same time frame.

As used herein, the phrase "efficacy window" describes a time frame during which an active agent exhibits a desired pharmacological effect, such as an antiviral effect, upon administration. In other words, this phrase describes that time period at which the plasma concentration of an active agent is equal to or higher than a minimal pharmacologically effective concentration thereof.

The phrase "substantially overlap" with respect to the efficacy windows of the active agents means that during a certain time period upon administration of two agents described herein (e.g., HCQ and GNS-227), both agents exhibit a desired pharmacological effect to some extent, namely, a plasma concentration of each agent is equal to or is higher than a minimum pharmacologically effective concentration of the agent. The efficacy windows of the active agents can overlap for, for example, 5 minutes, 10 minutes, 15 minutes, 20 minutes, 25 minutes, 30 minutes, 1 hour, 2 hours, 3 hours and even for longer time periods. The efficacy windows of the active agents can overlap such that during the overlapping period, both agents exhibit a maximal efficacy, such that one agent exhibits a maximal efficacy while the other agent exhibits a partial efficacy or such that both agents exhibit a partial efficacy.

In some embodiments, the method further comprises co-administering to the subject a therapeutically effective amount of an additional antiviral agent, which may or may not act in synergy with HCQ and/or GNS-227, such that at least 3 compounds are co-administered: HCQ, GNS-227 and one or more other antiviral agents.

Herein, the term "antiviral agent" encompasses any active compound or mixture of active compounds which is active against viruses, in particular HCV, and includes, but is not limited to, ribavirin and derivatives and prodrugs thereof (e.g., viramidine); interferons (e.g., interferon-α); viral protease inhibitors (e.g., boceprevir, SCH 503034, telaprevir, ITMN B, BILN 2061, SCH 6); NS4A inhibitors (e.g., GS-9132); NS5A inhibitors; viral polymerase inhibitors, including nucleoside and non-nucleoside polymerase inhibitors (e.g., NM-107 and its prodrug valopicitabine (NM-283), R1626/R1479, HCV-796, BILB 1941, R7128/PSI6130, GSK625433, A-848837, BCX-4678, GL59728, GL60667, NV-008, HCV-086, R803, JTK 003, XTL-2125); cyclophilin B inhibitors (e.g., alisporivir (DEBIO-025), NIM811); helicase inhibitors (e.g., QU665); glycosylation inhibitors (e.g., celgosivir (MX-3253)); an antiphospholipid antibody (e.g., bavituximab); and any combination thereof.

The term "anti-viral agent" as used herein encompasses prodrugs, pharmaceutically acceptable salts, hydrates, solvates and pharmaceutically active derivatives of any of the exemplary agents described herein.

Examples of antiviral agents suitable for use according to embodiments of the invention include:

PEGylated interferon alfa-2a (e.g., PEGASYS®); Interferon alfacon-1 (e.g., INFERGEN®); Natural interferon (e.g., OMNIFERON®); ALBUFERON®; Interferon beta-1a (e.g., REBIF®); Omega interferon (available from BioMedicine); Oral interferon alpha (available from Amarillo Biosciences); Interferon gamma-1b (available from InterMune); IP-501 (available from Interneuron); Merimedodib VX-497 (Vertex); Amantadine; IDN-6556 (Idun Pharma.); XTL-002 (XTL); HCV/MF59 (Chiron); Civacir (NABI); Viramidine (ICN); thymosin alfa-1 (e.g., ZADAXIN) (Sci Clone); histamine dihydrochloride (CEPLENE) (Maxim); VX 950/LY 570310 (Vertex/Eli Lilly); ISIS 14803 (Isis); IDN-6556 (Idun Pharma.); JTK 003 (AKROS Pharma); tarvacin (Peregrine); HCV-796 (ViroPharma); CH-6 (Schering); ANA971 (ANADYS); ANA245 (ANADYS); CPG 10101 (ACTILON) (Coley); rituximab; valopicitabine; HepX™-C antibody (XTL); IC41 (Intercell); Medusa Interferon (Flamel Technologies); E-1 (Innogenetics); Multiferon (Viragen); and BILN 2061 (Boehringer-Mannheim).

As used herein, the term "interferon" refers to a member of a family of highly homologous species-specific proteins that inhibit viral replication and cellular proliferation and modulate immune response. Herein, the term "interferon" encompasses derivatives of the naturally occurring proteins, including, without limitation, mutant forms of a naturally occurring interferon, and derivatives (e.g., conjugates) of a naturally occurring interferon, such as PEGylated interferon (polyethylene glycol modified conjugates of interferon) and interferon attached to another protein (e.g., as a fusion protein).

Human interferons are grouped into three classes based on their cellular origin and antigenicity: interferon-α (leukocytes), interferon-β (fibroblasts) and interferon-γ (B cells), each of which is encompassed herein by the term "interferon". Recombinant forms of each group have been developed and are commercially available. Subtypes in each group are based on antigenic/structural characteristics.

In exemplary embodiments, the interferon is an interferon-α.

Further according to an aspect of some embodiments of the present invention there is provided GNS-227 which is identified for use in combination with HCQ in the treatment of a hepatitis C virus (HCV) related disease. In some embodiments of this aspect of the present invention, the HCQ and the GNS-227 act in synergy, as defined herein in treating the disease (e.g., when co-administered as described herein).

According to embodiments of this aspect of the present invention the GNS-227 is for use in the treatment of an HCV-related disease, as described herein, wherein the treatment is effected by administering to a subject in need thereof, as described herein, HCQ in combination with GNS-227, wherein, in some embodiments, the HCQ and the GNS-227 act in synergy in treating the disease, as described herein.

According to these embodiments, the treatment comprises a synergistic combination of HCQ and the GNS-227, as defined herein.

Further according to an aspect of some embodiments of the present invention there is provided a use of GNS-227 in the manufacture of a medicament for use in the treatment of a hepatitis C virus (HCV) related disease in combination with HCQ. In some embodiments, the medicament is identified for use in treating an HCV related disease by administering to a subject in need thereof hydroxychloroquine in combination with GNS-227 that acts in synergy with HCQ (e.g., as described herein).

According to these embodiments, the treatment comprises a synergistic combination of HCQ and the GNS-227, as defined herein.

Further according to an aspect of some embodiments of the present invention there is provided hydroxychloroquine which is identified for use in combination with GNS-227 in the treatment of a hepatitis C virus (HCV) related disease. In some embodiments of this aspect of the present invention, the HCQ and the GNS-227 act in synergy, as defined herein in treating the disease (e.g., when co-administered as described herein).

According to embodiments of this aspect of the present invention the HCQ is for use in the treatment of an HCV-related disease, as described herein, wherein the treatment is effected by administering to a subject in need thereof, as described herein, HCQ in combination with GNS-227, wherein the HCQ and the GNS-227 act in synergy in treating the disease, as described herein.

According to these embodiments, the treatment comprises a synergistic combination of HCQ and the GNS-227, as defined herein.

Further according to an aspect of some embodiments of the present invention there is provided a use of a hydroxychloroquine in the manufacture of a medicament for use in the treatment of a hepatitis C virus (HCV) related disease in combination with GNS-227. In some embodiments, the medicament is identified for use in treating an HCV related disease by administering to a subject in need thereof hydroxychloroquine in combination with GNS-227 that acts in synergy with HCQ (e.g., as described herein).

According to these embodiments, the treatment comprises a synergistic combination of HCQ and the GNS-227, as defined herein.

In the medicaments described herein, the HCQ and GNS-227 can be co-formulated into a single pharmaceutical composition or can be used as two different compositions, optionally contained within a single kit or within two separate kits, as is further detailed hereinafter.

Suitable dosages (of HCQ and the GNS-227) for effecting synergy are described herein.

A therapeutically effective amount of an additional antiviral agent may optionally be co-administered with the HCQ and with the GNS-227 which acts in synergy with HCQ, as described elsewhere herein.

The methods and treatments (uses) described herein according to various aspects of the invention may comprise a step wherein one single pharmaceutical composition comprising hydroxychloroquine, or a pharmaceutically acceptable salt thereof, GNS-227, and optionally at least one pharmaceutically acceptable carrier, diluent, excipients and/or additive is administered. Alternatively, the methods and treatments (uses) of the invention may comprise a step wherein distinct compositions comprising at least one of the active ingredients cited above together with one or more acceptable carriers thereof, are administered substantially simultaneously or sequentially.

The combination of the invention may be preferably administered orally. The active combined drug compounds employed in the instant therapy can be administered in various oral forms including, but not limited to, tablets, capsules, pills, powders, granules, elixirs, tinctures, suspensions, syrups, and emulsions. It is contemplated that the active drug compounds can be delivered by any pharmaceutically acceptable route and in any pharmaceutically acceptable dosage form. These include, but are not limited to, the use of oral conventional rapid-release, time controlled-release, and delayed-release pharmaceutical dosage forms. The active drug components can be administered in a mixture with suitable pharmaceutical diluents, excipients or carriers (collectively referred to herein as "carrier" materials) suitably selected to with respect to the intended form of administration. As indicated, it is contemplated that oral administration can be effectively employed. Thus, tablets, capsules, syrups, and the like as well as other modalities consistent with conventional pharmaceutical practices can be employed.

According to another embodiment, the active ingredients used by the invention or composition comprising a combination thereof, may be administered via any mode of administration. For example, oral, intravenous, intramuscular, subcutaneous, intraperitoneal, parenteral, transdermal, intravaginal, intranasal, mucosal, sublingual, topical, rectal or subcutaneous administration, or any combination thereof.

Alternatively, the combination of this invention may also be administered in controlled release formulations such as a slow release or a fast release formulation. Such controlled release formulations of the combination of this invention may be prepared using methods well known to those skilled in the art. The method of administration will be determined by the attendant physician or other person skilled in the art after an evaluation of the subject's conditions and requirements.

The combined compounds of the present invention can be administered in the form of a pharmaceutical composition comprising both compounds of this invention together with a pharmaceutically acceptable carrier or diluent.

Since embodiments of the present invention relate to the treatment of diseases and conditions with a combination of active ingredients which may be administered separately, some embodiments of the invention also relate as a further aspect, to combining separate pharmaceutical compositions in a kit form. The kit includes two separate pharmaceutical compositions: hydroxychloroquine, or a pharmaceutically acceptable salt thereof, and GNS-227. The kit includes container means for containing both separate compositions; such as a divided bottle or a divided foil packet however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The kit may be for effecting any of the methods of treatment described herein, optionally with instructions describing how to effect the method.

It should be appreciated that both components of the kit, the hydroxychloroquine in the first dosage form and the GNS-227 in the second dosage form may be administered simultaneously.

Alternatively, HCQ or dosage form and GNS-227 or dosage form are administered sequentially in either order.

In any of the methods and used described hereinabove, administration of HCQ and GNS-227 is effected for a time period that optionally ranges from 1 month to life, optionally from 24 weeks to life, and optionally from 24 weeks to 1 year, depending on the HCV-related disease to be treated.

Generally, administration is effected as long as virus is found in the subject and/or until at least one of the symptoms associated with the disease are alleviated.

In embodiments where the HCV-related is chronic, treatment is effected for at least 24 weeks, as described herein.

According to further aspects of some embodiments of the present invention there are provided pharmaceutical kits.

In some embodiments, there is provided a kit comprising HCQ and GNS-227, each being individually packaged within the kit, wherein in some embodiments, the kit comprises instructions to use HCQ and GNS-227 in amounts in which synergy is exhibited, as defined herein.

In any of the methods, uses and kits described herein, the HCQ or a salt thereof and the GNS-227, if utilized, can be utilized either per se or can form a part of a pharmaceutical composition which further comprises a pharmaceutically acceptable carrier, as defined herein.

In any of the methods and uses described herein, the HCQ and GNS-227 can be formulated into a single pharmaceutical composition.

According to further aspects of embodiments of the present invention there is provided a pharmaceutical composition comprising HCQ (or a pharmaceutically acceptable salt thereof) and GNS-227, and a pharmaceutically acceptable carrier.

In some embodiments, the composition comprises an additional antiviral agent, as described herein. Such compositions may be formulated so as to be suitable for effecting a method of treatment described herein which comprises co-administration of HCQ and GNS-227, and optionally another antiviral agent.

Optionally, the composition is identified for use (e.g., in or on a packaging material) for use in treating an HCV-related disease.

In some embodiments, the composition is formulated for treating an HCV-related disease caused by an HCV genotype resistant to an antiviral agent (e.g., by sensitizing HCV to the antiviral agent), as discussed in more detail elsewhere herein.

In some embodiments, the composition is formulated so as to provide a synergistic effect between the HCQ and the antiviral agent, as discussed in more detail elsewhere herein.

In some embodiments, the composition is formulated so as to provide a desired overlapping efficacy window of the two agents. This can be achieved by formulating a composition for releasing a desired therapeutically effective amount of each agent (e.g., an amount for providing synergy) in a controlled manner.

The composition is preferably formulated for administration by a route suitable for both the HCQ and GNS-227.

As discussed herein, HCQ is suitable for oral administration. Furthermore, oral administration is a relatively convenient route of administration.

Hence, in some embodiments, the composition is formulated for oral administration.

In some embodiments, the composition is identified for use with an additional antiviral agent.

In some embodiments, the additional antiviral agent is unsuitable for inclusion in the composition, and as therefore administered separately. The additional antiviral agent may optionally be unsuitable for the route of administration of the composition, for example, wherein the composition is formulated for oral administration, and the additional antiviral agent is unsuitable for oral administration (e.g., an interferon).

Alternatively or additionally, additional antiviral agent may optionally be unsuitable for the frequency of administration of the composition, for example, wherein the composition is formulated for administration once per day, and the additional antiviral agent is more suitable for administration once per week (e.g., a PEGylated interferon-$\alpha$).

The composition may be, for example, in the form of a liquid, a semi-solid (e.g., gel), or solid.

In some embodiments, the composition is in a solid form. Examples of solid forms for a composition include, without limitation, a tablet, a capsule (e.g., comprising an encapsulated solid), a caplet, a powder, microspheroids, and granules.

The composition is preferably formulated in accordance with the intended frequency of administration of the composition. This, in turn, will depend on the properties of the active agents. As discussed herein, HCQ may be administered, for example, once per day, but also at other frequencies (e.g., twice or thrice a day).

It is to be appreciated that an active agent can be made more suitable for less frequent administration (e.g., once per day, as is particularly convenient, instead of twice or more per day) by formulating a composition appropriately, for example, by formulating the composition for slow release of the active agents therein.

Slow release preparations typically include slow release biodegradable carriers. Slow release biodegradable carriers are well known in the art. These are materials that may form particles that may capture therein an active compound(s) and slowly degrade/dissolve under a suitable environment (e.g., aqueous, acidic, basic, etc.) and thereby degrade/dissolve in body fluids and release the active compound(s) therein. The particles are preferably nanoparticles (i.e., in the nanometer range, e.g., in the range of about 1 to about 500 nm in diameter, preferably about 50-200 nm in diameter, most preferably about 100 nm in diameter).

The rate at which a drug is released is generally dependent on the rate at which the dosage form disintegrates or dissolves. Disintegration greatly increases the drug's surface area in contact with GI fluids, thereby promoting drug dissolution and absorption. Disintegrants and other excipients (e.g., diluents, lubricants, surfactants, binders, dispersants) are often added during manufacture to facilitate these processes. Surfactants increase the dissolution rate by increasing the wettability, solubility, and dispersibility of the drug. Disintegration of solid forms may be retarded by excessive pressure applied during the tableting procedure or by special coatings applied to protect the tablet from the digestive processes of the gut. Hydrophobic lubricants (e.g., magnesium stearate) may bind to the active drug and reduce its bioavailability.

Dissolution rate determines the availability of the drug for absorption. When slower than absorption, dissolution becomes the rate-limiting step. Overall absorption can be controlled by manipulating the formulation. For example, reducing the particle size increases the drug's surface area, thus increasing the rate and extent of GI absorption of a drug whose absorption is normally limited by slow dissolution. Dissolution rate is affected by whether the drug is in salt, crystal, or hydrate form.

Oral slow-release forms are often designed to maintain therapeutic drug concentrations for greater than 12 hours. The absorption rate can be controlled by coating drug particles with wax or other water-insoluble material, by embedding the drug in a matrix from which it is released slowly during transit through the GI tract, or by complexing the drug with ion-exchange resins.

Thus, for example, a slow-release formulation in tablet form, may be based on the use of a hydrophilic polymer which swells in contact with gastrointestinal fluids, to form a gel, which creates a barrier that enrobes the tablet. The barrier limits physical exchanges between the inside of the tablet and the surrounding medium. As a consequence, intrusion of water towards the tablet matrix and diffusion of drug are slowed down, allowing a controlled slow release of the drug.

Various types of polymers may be used as a matrix for the slow-release of drugs, such as polyvinyl chloride, polyethylene polyamides, ethylcellulose, silicone, poly (hydroxyethyl methacrylate), other acrylic co-polymers, and polyvinylacetate-polyvinyl chloride copolymers.

In some embodiments, the composition is a unit dosage form (e.g., a unit dosage form formulated for oral administration).

The term "unit dosage form", as used herein, describes physically discrete units (e.g., in solid form), each unit containing a predetermined quantity of HCQ and GNS-227 calculated to produce the desired therapeutic effect, in association with at least one pharmaceutically acceptable carrier, diluent, excipient, or combination thereof (e.g., as described herein).

The amount of HCQ and GNS-227 in the composition are optionally adjusted so as to provide an appropriate amount of each active agent per day (e.g., as described elsewhere herein).

Optionally, each unit dosage form comprising a therapeutically effective amount of HCQ, as described hereinabove, suitable for 1 day (e.g., from 400 to 2000 mg, from 500 to 1000 mg, etc.) and a therapeutically effective amount of GNS-227. Optionally, such a pharmaceutical composition is further identified for administration once per day.

Alternatively, each unit dosage form comprises one half of a therapeutically effective amount of HCQ, as described hereinabove, suitable for 1 day (e.g., from 200 to 1000 mg, from 250 to 500 mg, etc.) and one half of a therapeutically effective amount of GNS-227, as described herein. Optionally, such a pharmaceutical composition is further identified for administration twice per day.

The unit dosage forms described herein may be provided together in a kit which comprises discrete unit dosage forms described herein, packaged together in a packaging material.

Techniques for formulation and administration of drugs may be found in "Remington's Pharmaceutical Sciences" Mack Publishing Co., Easton, Pa., latest edition, which is incorporated herein by reference.

Pharmaceutical compositions of embodiments of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with embodiments of the present invention thus may be formulated in conventional manner using one or more pharmaceutically acceptable carriers comprising excipients and auxiliaries, which facilitate processing of the active ingredients (HCQ and antiviral agents described herein) into preparations which, can be used pharmaceutically. Proper formulation is dependent upon the route of administration chosen.

For injection, the active ingredient(s) of embodiments of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the active ingredients can be formulated readily by combining the active ingredients described herein with pharmaceutically acceptable carriers well known in the art. Such carriers enable the active ingredient(s) to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredients.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients described herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active ingredient(s for use according to embodiments of the present invention are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient(s and a suitable powder base such as, but not limited to, lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active ingredients. Additionally, suspensions of the active ingredients may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredients to allow for the preparation of highly concentrated solutions.

Alternatively, the active ingredients may be in powder form for constitution with a suitable vehicle, e.g., sterile, pyrogen-free water, before use.

The active ingredients of embodiments of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Compositions comprising HCQ and GNS-227, as described herein, formulated in a compatible pharmaceutical carrier may also be prepared, packaged in a packaging material, and identified in or on the packaging material, for treatment of an HCV-related disease, as is detailed herein.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Synthesis of GNS-227

Materials and Experimental Methods:

Reagents and solvents were obtained from commercial suppliers and were used without further purification, unless otherwise indicated.

Methylene chloride was dried and distilled over CaCl2 and stored over molecular sieves 4 Å under argon.

Tetrahydrofuran was dried over sodium/benzophenone ketyl under argon and distilled prior to use.

Flash chromatography purifications were performed on Macherey Nalgel silica gel (40-63 μM) as the stationary phase or were conducted using packed RediSep® columns on a Teledyne Isco Combiflash® Companion® apparatus.

Analytical High Performance Liquid Chromatography-Mass Spectrum Analysis (HPLC-MS):

HPLC-MS conditions A1: HPLS-MS were performed on a Waters Alliance 2790 apparatus equipped with Photodiode Array Detector Waters 996 and a Waters Micromass Q-T of using a BDS Hypersil 50×2.1, 3 μm. Eluting conditions comprised a linear gradient: 0% to 80% of MeCN/H$_2$O in 20 minutes (containing 0.1% TFA in positive mode and without TFA in negative mode), flow rate 0.2 mL/minute.

HPLC-MS conditions A2: HPLS-MS were performed on a Waters Alliance 2790 apparatus equipped with Photodiode Array Detector Waters 996 and a Waters Micromass Q-T of using a Nucleodur C18 Pyramid 50×2.1, 3 μm. Eluting conditions comprised a linear gradient: 0% to 80% of MeCN/H$_2$O in 20 minutes (containing 0.1% TFA in positive mode and without TFA in negative mode), flow rate 0.3 mL/minute.

HPLC-MS conditions B: HPLS-MS were performed on a Agilent HP-1100 apparatus equipped with Photodiode Array Detector Agilent G1315A, a polymerlabs ELS2100 (DEDL) detector and a Agilent Simple Quad ESI for mass analysis using a Agilent Zorbax XDB-C18 RP C18 45×4.6, 3.5 μm. Eluting conditions comprised a linear gradient: 10% to 100% in 4.5 minutes of MeCN/H$_2$O (containing 0.05% TFA), flow rate 1.5 mL/minute.

Low resolution mass spectra (MS) were obtained from an Applied Biosystems SCIEX 3200 QTRAP in Atmospheric Pressure Ionization condition (API) in positive (ES+) or negative (ES−) mode.

High Resolution Mass Spectroscopy (HRMS) was obtained from a Perkin Elmer apparatus.

NMR spectra were recorded on Bruker Avance 250 at 250 MHz for $^1$H and 63 MHz for $^{13}$C NMR in deuterared solvents and are referenced in ppm relative to the solvent residual peak [see Gottlieb H. E. et al. *J. Org Chem* 1997 (2) 7512-7515].

Synthesis of a Hydroxyproline Derivative:

An exemplary synthetic pathway for preparing a hydroxyproline derivatized (e.g., esterified) by a tetrahydroindole-containing moiety is presented in Scheme 1 below.

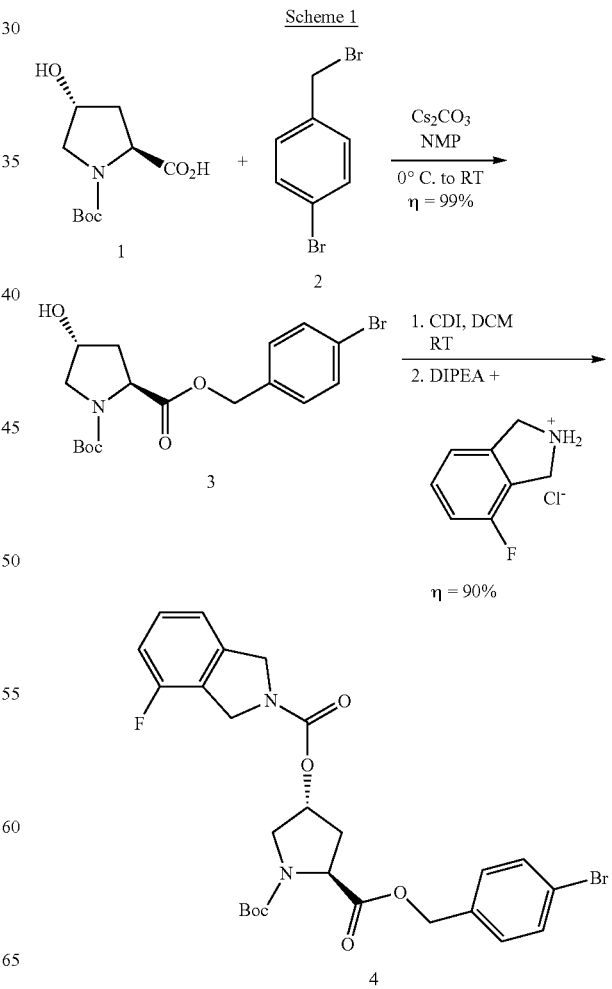

25
-continued
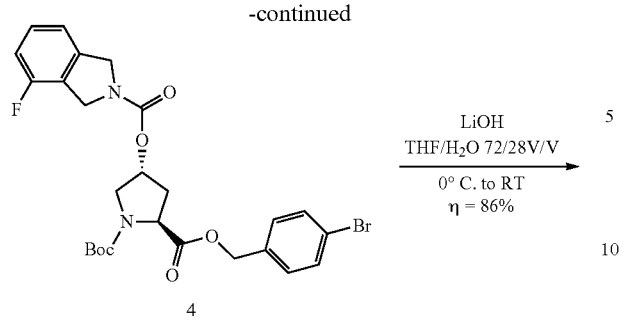
26
-continued
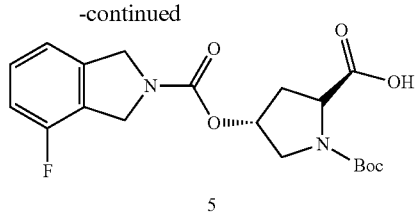
Synthesis of GNS-227 (Compound 10):
GNS-227 was prepared following the synthetic pathway depicted in Scheme 2 below.
Scheme 2
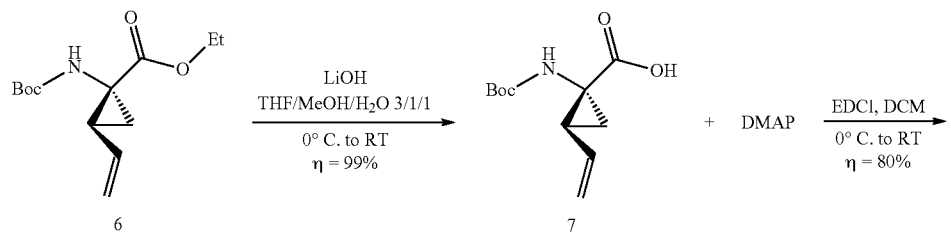
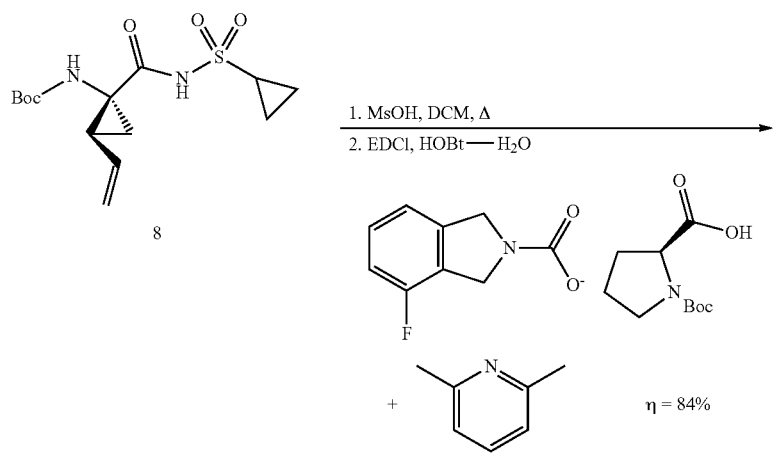
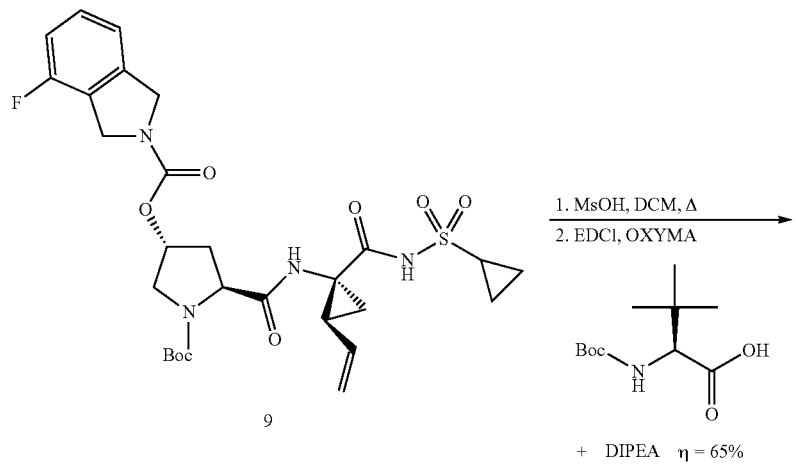

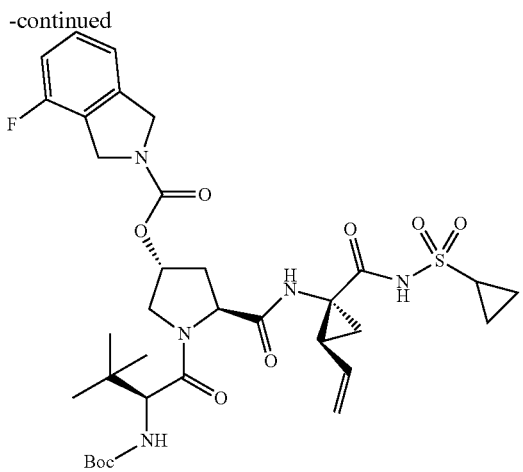

10

Example 2

Antiviral Activity

GNS-227 (Compound 10) was found to exhibit inhibition activity on various proteases and was further tested for its effect, either alone or in combination with hydroxychloroquine on HCV replication using the HCV replicon model as follows.

Material and Methods:

GNS-227 was prepared as described in Example 1 hereinabove.

Hydroxychloroquine sulfate was obtained from Sigma.

Culture and Treatment of Huh7 Cells:

Huh7 cells were maintained at 37° C., in an atmosphere of 5% $CO_2$, in DMEM (Dulbecco's modified Eagle medium) supplemented with 2 mM L-glutamine, non-essential amino acids (NEAA), 10% fetal bovine serum (FBS) and 500 mg/ml geneticin. Cells were sub-divided at a 1:3 or 1:4 ratio every 2-3 days. 24 hours prior to the assay, Huh7 cells were collected, counted, plated in 96-well plates at 7,500 cells/well in 100 ml standard maintenance medium, and incubated in the conditions above. To initiate the assay, culture medium was removed, and cells were washed once with PBS (phosphate buffer saline). For control compounds only, 90 ml assay medium (DMEM with L-glutamine, NEAA, and 10% FBS) was added.

Test compounds were prepared as a 10× stock in assay medium. Serial dilutions of compounds in assay medium were added in a total volume of 10 μA and the plates were then rocked to mix, and incubated as described above for 72 hours.

Quantification of HCV Levels:

HCV RNA levels were measured using TaqMan® RT-PCR. Total cellular RNA was isolated and amplified by using a RealTime HCV assay (m1000™ Automated Sample Preparation System and M2000rt™ instrument for reverse transcription, PCR amplification, and detection/quantitation, Abbott Molecular Inc.), which detects and quantitates HCV genotypes 1-6. The molecular genotyping method targets the 5'-untranslated (UTR) region of the virus genome and is based on an amplification of the viral genome. An internal control, simultaneously amplified by RT-PCR, served to demonstrate that the process proceeded correctly for each sample. A negative control, low positive control and high positive control were also introduced. Results are reported in International Units per ml (IU/ml), and 1 IU/ml=4.3 copies/ml. The lower limit of detection was 12 IU/ml with ≥95% probability. The dynamic range of the assay extended from 12 to 100,000,000 IU/ml. The $EC_{50}$ was defined as the concentration of compound at which the HCV RNA level in the replicon cells was reduced by 50%.

Quantification of Cytotoxicity:

In order to measure any cytotoxic effect, the viabilities of the replicon cells following 72 hours of treatment with a tested compound were determined using an MTS (3-[4,5-dimethylthiazol-2-yl]-5-[3-carboxymethoxyphenyl]-2-[4-sulfophenyl]-2H tetrazolium inner salt) assay (CellTiter 96® AQueous One Solution Cell Proliferation Assay; Promega). The $CC_{50}$ was defined as the concentration of the compound at which cell viability was reduced by 50%.

Analysis of Antiviral Drug Combinations:

Antiviral assays were performed by treating Huh7 cells with a combination of hydroxychloroquine and GNS-227, as described hereinabove for Huh7 cells. Each combination of drugs was assayed in triplicate.

The effects of drug combinations were evaluated according to the method described by Prichard & Shipman [*Antiviral Res* 1990, 14:181-205]. The theoretical additive effect was calculated from the dose-response curves of individual compounds by the equation Z=X+Y(1−X) (an equation referred to in the art as a Bliss independence model), where X and Y represent the inhibition produced by the individual compounds and Z represents the theoretical effect produced by the combination of compounds. The experimental results were normalized to the theoretical results expected for an additive effect (i.e., "Z"), and the theoretical additive surface was then subtracted from the actual experimental surface, to obtain a horizontal surface which represents synergy between the drugs. Thus, when the surface equals the zero plane, the combination is additive rather than synergistic. A surface that lies above the zero plane (e.g., at least 20%) indicates a synergistic effect of the combination and a surface lower than the zero plane (e.g., below minus 20%) indicates antagonism between the drugs.

The effects of drug combinations were also evaluated by calculating a Combination Index (CI) for three different drug ratios in a Loewe additivity model, using CalcuSyn software based on the method described by Chou & Talalay [*Trends Pharmacol Sci* 1983, 4:450-454], and using NPTII enzyme-linked immunosorbent assay. CI values of <1, 1, and >1 indicate synergy, an additive effect, and antagonism, respectively.

The effects of drug combinations were also evaluated by standard isobologram analysis, using CalcuSyn software.

Results:

Huh7 cells were treated with various concentrations (0, 0.22, 0.66, 2, 6 and 18 μM) of hydroxychloroquine sulfate (HCQ), dissolved in water in combination with various concentrations (0, 0.41, 3.7, 11.1, 33.3, 100 et 300 nM) of GNS-227 dissolved in DMSO, as described hereinabove. The levels of HCV RNA were measured by RT-PCR, and the results were analyzed according to Prichard-Shipman, Chou-Talalay and isobologram models, as described hereinabove. In addition, cytotoxicity of the tested combinations of HCQ and GNS-227 was determined as described hereinabove.

As shown in FIG. 1, HCQ and GNS-227 exhibited a synergistic effect in combination, as determined according to a Prichard-Shipman model. The synergistic effect was particularly pronounced for a combination of between 0.41 and 11.1 nM GSN-227 and between 0.66 and 6 μM HCQ, for which the inhibition of HCV was at least 20% more than expected for an additive effect, with the highest synergistic effect exhibited for a combination of 3.7 nM and 6 μM HCQ.

The data shown for the Bliss independence modeling of variable drug ratio combinations, presented in FIG. 2, was in corroboration with the Prichard-Shipman model.

Table 1 presents the Combination Index (CI) values for combinations of hydroxychloroquine (HCQ) and GNS-227 calculated according to a Chou-Talalay model.

As shown in Table 1, HCQ and GNS-227 exhibited a synergistic effect in combination, with the calculated combination index values all being considerably lower than 1.

TABLE 1

| GNS-227 (Nm):HCQ (μM) | Combination Index | | |
| --- | --- | --- | --- |
| ratio | $ED_{50}$ | $ED_{75}$ | $ED_{90}$ |
| 6:1 | 0.51 | 0.54 | 0.57 |
| 2:1 | 0.45 | 0.49 | 0.55 |
| 1:2 | 0.52 | 0.54 | 0.56 |

$ED_{50}$, $ED_{75}$ and $ED_{90}$ represent amount of drug which result in 50%, 75% and 90% inhibition of viral activity.

As shown in FIG. 3, HCQ and GNS-227 exhibited a synergistic effect in combination, as determined by an isobologram.

The agreement between the various models indicates that hydroxychloroquine and GNS-227 exhibit a considerable synergistic effect when administered in combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a hepatitis C virus (HCV) infection in a subject in need thereof, the method comprising co-administering to the subject a therapeutically effective amount of hydroxychloroquine or a pharmaceutically acceptable salt thereof in combination with a therapeutically effective amount of the compound GNS-227:

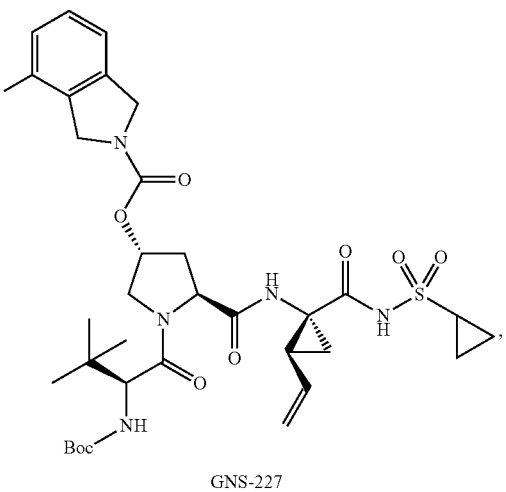

GNS-227 thereby treating the HCV infection, wherein said therapeutically effective amount of hydroxychloroquine and said therapeutically effective amount of said GNS-227 are selected such that said hydroxychloroquine and said GNS-227 act in synergy in reducing HCV replication.

2. The method of claim 1, wherein said therapeutically effective amount of hydroxychloroquine is in a range of from 100 to 2000 mg per day.

3. The method of claim 2, wherein said therapeutically effective amount of hydroxychloroquine is in a range of from 800 to 1000 mg per day.

4. The method of claim 1, wherein said HCV infection is a chronic HCV infection.

5. The method of claim 1, wherein said HCV infection is caused by an anti-viral resistant genotype of said HCV.

6. The method of claim 1, further comprising co-administering to the subject of a therapeutically effective amount of an additional antiviral agent.

7. A pharmaceutical composition comprising hydroxychloroquine or a pharmaceutically acceptable salt thereof, a compound GNS-227:

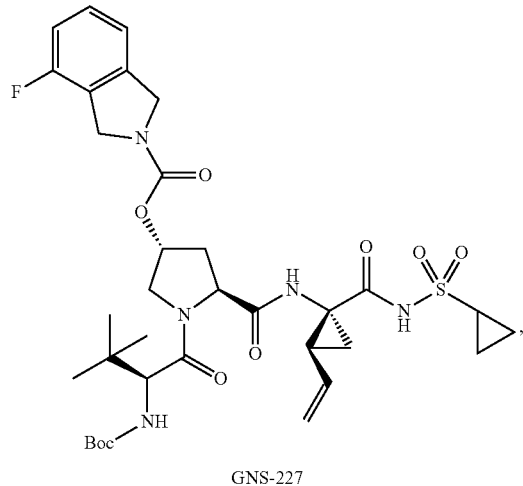

GNS-227 and a pharmaceutically acceptable carrier.

8. The composition of claim 7, being formulated for oral administration.

9. The composition of claim 8, being in a solid form.

10. The composition of claim 7, being a unit dosage form of the composition.

11. A pharmaceutical composition unit dosage form comprising hydroxychloroquine or a pharmaceutically acceptable salt thereof, the compound GNS-227:

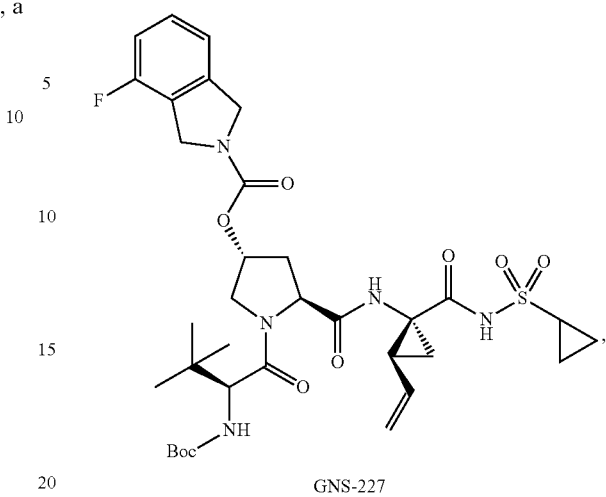

GNS-227 and a pharmaceutically acceptable carrier.

12. The unit dosage form of claim 11, being formulated for oral administration.

13. The unit dosage form of claim 12, being in a solid form.

14. The unit dosage form of claim 11, wherein an amount of hydroxychloroquine and an amount of said GNS-227 are selected such that said hydroxychloroquine and said GNS-227 act in synergy in reducing HCV replication.

15. The unit dosage form of claim 11, wherein an amount of hydroxychloroquine is in a range of from 100 to 2000 mg, the unit dosage form being identified for administration once per day.

16. The unit dosage form of claim 11, wherein an amount of hydroxychloroquine is in a range of from 50 to 1000 mg, the unit dosage form being identified for administration twice per day.

* * * * *